(12) United States Patent
Brugger et al.

(10) Patent No.: US 6,878,145 B2
(45) Date of Patent: Apr. 12, 2005

(54) COMPONENT OF A LASER TREATMENT DEVICE AND LASER TREATMENT DEVICE WITH A LIGHTING SYSTEM

(75) Inventors: Wilhelm Brugger, Bürmoos (AT); Anton Kasenbacher, Traunstein (DE); Mark Niemz, Sinzheim (DE); Martin Strassl, Bürmoos (AT)

(73) Assignee: W & H Dentalwerk Burmoos GmbH (AT)

( * ) Notice: Subject to any disclaimer, the term of this patent is extended or adjusted under 35 U.S.C. 154(b) by 0 days.

(21) Appl. No.: 10/381,999
(22) PCT Filed: Mar. 28, 2002
(86) PCT No.: PCT/EP02/03545
  § 371 (c)(1),
  (2), (4) Date: Jun. 9, 2003
(87) PCT Pub. No.: WO02/080803
  PCT Pub. Date: Oct. 17, 2002

(65) Prior Publication Data
  US 2004/0097910 A1 May 20, 2004

(30) Foreign Application Priority Data
  Apr. 6, 2001 (DE) .......................................... 101 17 347

(51) Int. Cl.⁷ ............................................... A61B 18/20
(52) U.S. Cl. ........................................... 606/18; 433/29
(58) Field of Search ........................... 606/2–19; 433/29

(56) References Cited

U.S. PATENT DOCUMENTS

| | | | | | |
|---|---|---|---|---|---|
| 4,582,405 | A | * | 4/1986 | Muller et al. ................ | 351/221 |
| 4,644,948 | A | * | 2/1987 | Lang et al. ..................... | 606/4 |
| 4,830,483 | A | * | 5/1989 | Kohayakawa et al. ......... | 606/4 |
| 5,071,417 | A | | 12/1991 | Sinofsky | |
| 5,076,685 | A | * | 12/1991 | Muller et al. ................ | 351/221 |
| 5,280,378 | A | * | 1/1994 | Lombardo ................... | 359/199 |
| 5,616,141 | A | * | 4/1997 | Cipolla ........................ | 606/15 |
| 5,645,550 | A | * | 7/1997 | Hohla ......................... | 606/108 |
| 5,865,829 | A | * | 2/1999 | Kitajima ........................ | 606/3 |
| 6,135,774 | A | * | 10/2000 | Hack et al. ................. | 433/215 |
| 2001/0041884 | A1 | * | 11/2001 | Frey et al. .................... | 606/5 |
| 2003/0036751 | A1 | * | 2/2003 | Anderson et al. ............. | 606/9 |

FOREIGN PATENT DOCUMENTS

| | | | | |
|---|---|---|---|---|
| DE | 3319203 A1 | 5/1983 | ............. | A61F/9/00 |
| WO | WO 01/19454 A2 | 2/2005 | | |

* cited by examiner

*Primary Examiner*—Roy D Gibson
*Assistant Examiner*—Henry M Johnson, III
(74) *Attorney, Agent, or Firm*—Leonard J. Santisi; Frommer Lawrence & Haug

(57) ABSTRACT

Laser treatment appliance having an illumination system, in particular for use in the field of medicine, has a laser light source for producing a treatment laser beam which is guided essentially freely, as well as an illuminating light source for producing a visible light for illuminating an area to be treated, and one or more first optical elements via which the treatment laser beam is passed on, with at least one of the first optical elements being in the form of an optical multi-function element, such that the visible light for illumination is also steered at least over this at least one optical multi-function element. The laser treatment appliance furthermore has an optical evaluation apparatus for diagnosis or analysis of radiation which is produced during the treatment process, and all the optical multifunction elements are designed such that they influence the treatment laser beam and the visible illuminating light essentially in an equivalent reflecting and/or transmitting manner. The laser treatment appliance furthermore has a beam splitter, which extends at least over the entire cross section of the treatment laser beam, for outputting the radiation, and which is arranged between the laser light source and the first multifunction element in the incidence direction of the treatment laser beam such that the visible light from the illuminating light source does not pass through it.

12 Claims, 3 Drawing Sheets

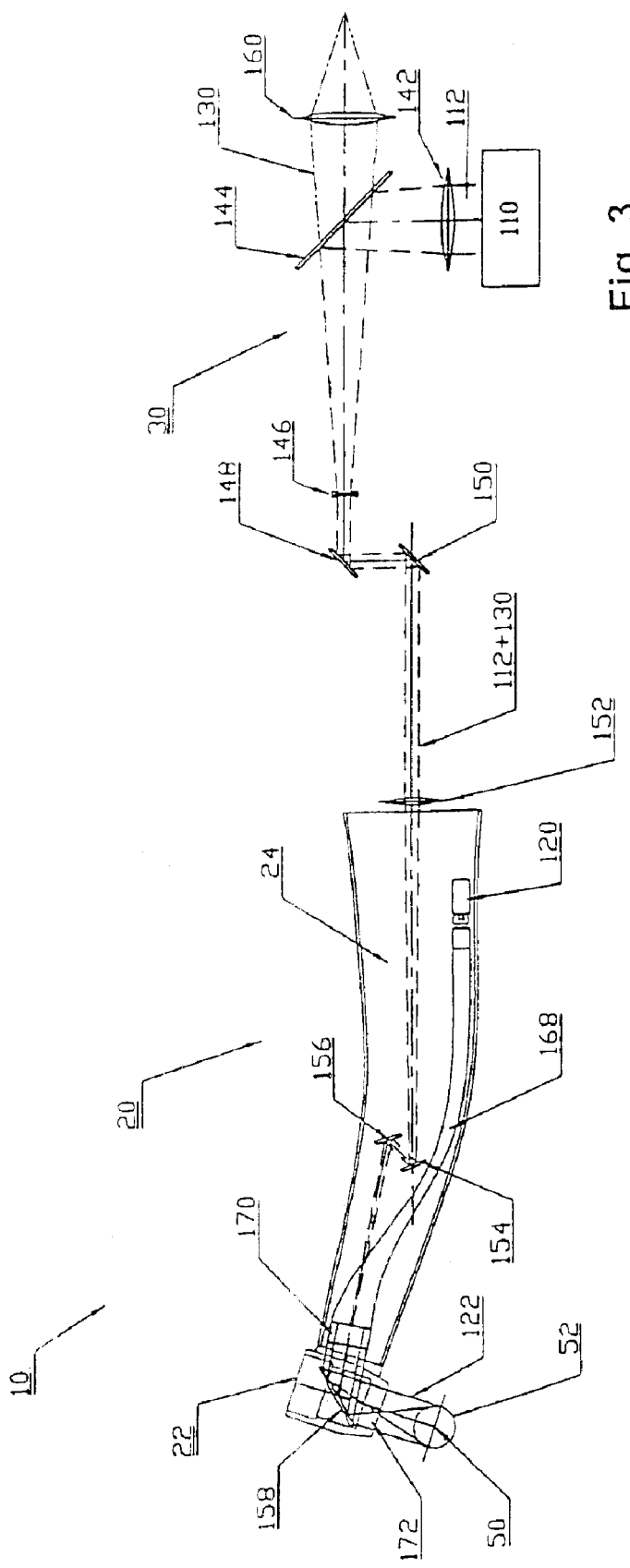

COMPONENT OF A LASER TREATMENT DEVICE AND LASER TREATMENT DEVICE WITH A LIGHTING SYSTEM

The present invention relates to a component of a laser treatment appliance having an illumination system, in particular for use in the field of medicine, with the laser treatment appliance having a laser light source for producing a treatment laser beam, and an illuminating light source for producing visible light for illuminating an area to be treated, and with the component having one or more first optical elements, via which the treatment laser beam is passed on. The invention furthermore relates to a laser treatment appliance having an illumination system, especially for use in the field of medicine, having a laser light source and an illuminating light source.

BACKGROUND

Various treatment appliances are known in particular from the field of dentistry, in which both treatment appliances having mechanical treatment elements, such as a drill, and treatment appliances which use a laser beam instead of the mechanical treatment elements are used.

Depending on the field of application, it is advantageous or necessary to illuminate the area to be treated, in order to create suitable lighting conditions for the operator of the appliances. Particularly in areas where access is difficult, as is the case especially in the field of dentistry, it is frequently difficult to illuminate the area to be treated using external illumination sources, in particular because the treatment or processing appliance, and/or the operator himself, shadows the area to be treated.

Appliances are therefore known from the prior art in which illumination apparatuses which are designed integrally with the treatment appliance are provided. By way of example, one prior art reference discloses a dentistry handpiece, which has a treatment head to which a mechanical treatment tool is fitted. The handpiece furthermore has an optical fiber, which is passed through the handpiece and is passed out of the handpiece at the side, close to the treatment tool, so that the treatment tool as well as the area to be treated can be illuminated by means of an illuminating light source.

Another prior art reference discloses a tartar removal tool, which, has a treatment tool in a front region, in this case a tartar removal tool, which is caused to oscillate. An optical fiber is passed through the handpiece in the apparatus disclosed in this document as well, with the optical fiber opening in the vicinity of the treatment tool, and being intended to illuminate the area to be treated, by means of an illuminating light source.

The known illumination systems according to the prior art have the disadvantage that the supply for the optical fiber is relatively complex and hence costly, with the optical fiber also being relatively sensitive, which, over the course of the life of a corresponding appliance, can lead to decreases in the illumination light intensity that is available. Furthermore, if the optical fiber is destroyed, the entire optical fiber must be replaced, which is highly costly or, in some circumstances, is no longer financially possible at all.

Furthermore, depending on the treatment tool, the illumination of the area to be treated is not optimum, as is the case especially with drills, in which the light is supplied through an optical fiber fitted at the side.

A further prior art reference discloses a method and an apparatus for dose measurements for photocoagulation, in which monochromatic laser light coming from a laser, on the one hand, and light from a lamp for object illumination, on the other hand, are passed via a chromatic beam splitter onto a sample, with the chromatic beam splitter being permeable to the light from the lamp for object illumination, that is to say having a transmitting effect, while the beam splitter acts as a reflector for the laser light. Fluorescent light emerging from the sample is at least partially emitted through a beam splitter, which is transparent for this fluorescence light but is reflective for the light from the lamp for object illumination, so that at least a portion of the fluorescence light can be evaluated using a photomultiplier.

A further prior art reference discloses a laser apparatus in which, in addition to a laser diode for producing laser light, there is also a diode for producing a so-called "guide light". The light from the two light sources is also in this case injected via a monochromatic beam splitter, with the beam splitter being completely reflective for the so-called guide light.

These systems according to the prior art have, in particular, the disadvantage that, in the case where the radiation produced during the treatment process or the spectroscopic light is in a wavelength band, which corresponds to the wavelength band of the illuminating light, or overlaps it, diagnosis or analysis is impossible, or is feasible only with very great difficulty, especially in the case of weak radiation and/or weak spectroscopic light, since the spectroscopic light cannot be emitted, or can be emitted only inadequately, in the at least overlapping wavelength band.

One object of the present invention is thus to provide a laser treatment appliance having an illumination system, which avoids the abovementioned disadvantages of the prior art and, in particular, provides an effective illumination system and an effective capability for diagnosis or analysis of the treatment process, in a simple and cost-effective manner.

This object is achieved by a laser treatment appliance with the particularly advantageous embodiments of the laser treat appliance according to the invention.

SUMMARY OF THE INVENTION

According to the invention, the laser treatment appliance thus has one or more optical multifunction elements, which are all designed such that they essentially have a comparable influence on the treatment laser beam on the one hand and on the visible light for illumination on the other hand, in which case this should be understood as meaning that the multifunction elements are either reflective for the wavelengths of both the treatment laser beam and of the visible illuminating light, or else are designed to be transmissive for both wavelengths or wavelength bands, so that the optical multifunction elements according to this invention are not chromatic beam splitters, as were regarded as being necessary in the prior art until now, at least for injecting and joining together the treatment laser beam and the illuminating light.

The configuration of the laser treatment appliance according to the invention thus firstly makes it possible for the first optical elements (which are required in any case in order to steer the treatment laser beam produced by the laser light source onto the area to be treated) are at least partially likewise used for steering visible light from the illuminating light source onto the area to be treated, while secondly allowing radiation which is produced during the treatment process to be supplied in an effective manner to the optical evaluation apparatus, in particular to a spectrometer, with losses being avoided.

Furthermore, the first optical elements for guiding or steering, directing the treatment laser beam are generally very high-quality optical elements, so that the illuminating light can also be passed on very effectively. For cost reasons, such high quality elements are generally not used for illumination, so that the present invention at the same time results in a double effect, firstly a cost reduction, since optical elements are spared, and secondly a qualitative improvement, since very high quality optical elements can also be used for the visible illuminating light.

At this point, it should be noted that the wavelength of the treatment laser beam is generally not in the visible band. Owing to the different geometric configurations and focussing of the treatment laser beam in comparison to desired illuminating light, however, the laser beam is in principle not suitable for illuminating the area to be treated, irrespective of its wavelength, since the treatment laser beam must generally be focussed at a treatment point, while the illuminating light is intended to illuminate a larger area around the point to be treated as uniformly as possible.

The same also applies to any so-called pilot laser beams which may be used to emit light in the visible band and are used as an "aiming apparatus" in order to indicate to the operator the point on the material to be treated at which the treatment laser beam is acting or will act, with this treatment laser beam possibly being invisible to the user.

Irrespective of the focussing, a pilot laser beam such as this would not be suitable for use as illuminating light even if it were optically broadened since, in a case such as this, the high coherence length would lead to destructive interference phenomena on the surface of the material to be treated, resulting in the production of so-called speckles, which appear as black or dark spots in the illuminated area and thus prevent undisturbed identification of details, which is actually the aim of the illumination to avoid. The appearance of speckles can lead to the identification of details frequently being considerably poorer than without the possibly widened pilot laser beam. The same applies analogously to any laser light source which may be present and is used for diagnosis purposes, for example for stimulation of fluorescence.

For the purposes of the invention, the expression "optical elements" should be understood as meaning all known optical elements in the widest sense, not only elements which influence the profile of the light or of the laser beam, such as steering, focussing, reflecting elements, or elements which influence the incident light in some other way. Furthermore, for the purposes of the invention the expression "optical elements" also covers elements which do not significantly influence the profile of the light which strikes them or of a treatment laser beam, such as outlet apertures or termination plates, which are essentially completely transmissive for the wavelength of the corresponding light. In addition, no deflection or bending takes place when passing through such an optical element (or such deflection is negligible). Optical elements may, in particular, be mirrors, waveguides, optical fibers, such as glass fibers, covering windows or outlet windows.

Furthermore, it shall be mentioned that an optical element may also have different areas, with different affects in these areas. For the purposes of the invention, an optical element may be, for example, a mirror which is designed to be essentially planar over a wide region, but which is curved in an edge area. In principle, it is also possible for an optical element to have clear boundaries between the various areas, such as edges or coatings, and, for example, even non-reflective coatings. Furthermore, it is possible for an optical element also to be split in two, for the purposes of the invention, in order to produce the desired effects.

For the purposes of the invention, both a simple laser such as a diode laser and a complex laser apparatus, which may possibly also have a number of individual lasers, should be regarded as a "laser light source", for example having an associated pump laser in addition to the laser which produces the treatment laser light. For the purposes of the invention, the laser light source may also have any associated appliances, such as frequency converters, etc.

For the purposes of the invention, the expression "illuminating light source" should be understood as meaning a light source which does not exclusively emit essentially monochromatic light, such as laser light. An illuminating light source such as this may comprise one or more in principle undefined light sources, but it is also possible for only one apparatus to be regarded as an illuminating light source for the purposes of the invention, which introduces or injects light into the laser treatment appliance from some other source, which need not be part of the laser treatment appliance. This also includes, for example, a mirror apparatus which uses daylight or external light for illumination, and which likewise satisfies the desired requirements. It is preferable for the illuminating light source to emit white light in a preferred manner, preferably at least composed of at least two, and especially at least three, central wavelengths, whose coherence length is chosen appropriately in order to avoid, in particular, the abovementioned speckles, which do not allow effective illumination. In particular, an illuminating light is desirable which has a very broadband frequency or wavelength distribution. In particular, illuminating light sources are preferably used which comply with the requirements of the DIN Standards for workplace illumination, in particular with DIN Standard 5035 (in particular Part 1) and 6169 (in particular Parts 1 and 2), whose entire contents are included by direct reference in this application.

In one preferred embodiment, the component according to the invention is designed such that the treatment laser beam which is carried in it is guided essentially freely. Free guidance of the laser beam should be understood as meaning extensive guidance in an essentially free interior of the component, which may be filled with air or a gas, and which may possibly also be at a reduced pressure or maybe a vacuum. The guidance of the laser beam in this free interior of the component is steered and aligned or focussed by means of the first optical elements mentioned above, in particular, by means of mirrors and lenses as well as windows.

In one such embodiment, an extremely large number of degrees of freedom are available both for the treatment laser beam and for additional guidance of the visible light for illumination, likewise in the interior of the component, and in particular using as many first optical elements as possible.

The component preferably also has a first optical element, which is essentially in the form of an outlet window which is designed to be transmissive for the laser treatment light and which does not significantly influence the profile of the treatment laser beam. An outlet window such as this is generally provided for termination of the treatment end of the component, in particular of the handpiece, in order to shield the interior from the outside. If the illuminating light is likewise passed through this outlet window, this results especially in highly effective illumination, since the visible light for illumination is emitted essentially from the same direction and parallel, as well as preferably in the same spatial area as the treatment laser beam. Thus shadowing is avoided even in areas where access is very difficult, especially in the field of dentistry, with root treatment being mentioned in particular, here, by way of example.

In addition to the described embodiment, in which the outlet window of the component is in the form of an optical multifunction element, an embodiment is, of course, also feasible in which, in addition to the outlet window, an inlet window of such a component may also be in the form of an optical multifunction element for passing on or steering both the treatment laser beam and the visible light for illumination.

However, it is particularly preferable for such first optical elements to be in the form of optical multifunction elements, which not only shield a specific spatial area and do not significantly influence the treatment laser beam and/or the visible light for illumination, but which are in the form of elements which influence the treatment laser beam and/or the visible light for illumination. These include lenses which focus, broaden or in some other way influence light passing through them, or mirror elements, which steer the laser beam in the desired direction, especially in the internal area of the component with a laser beam which is guided freely, in which case such mirrors may likewise have focusing or widening functions. This makes it possible for the visible light for illumination to take a path through the component whose route is similar, at least in large areas, to the predetermined route of the treatment laser beam. No additional elements are required for steering or influencing the visible light.

The greater the extent to which the first optical elements for the treatment laser beam are in the form of optical multifunction elements, the fewer additional optical elements are required, and these are provided only for the visible light for illumination.

In a further preferred embodiment of the component according to the invention, this component has an optical element for injecting the illuminating light into the component. An optical element such as this is required when the illuminating light source is not provided in the component, with the component thus being a centerpiece or an end piece at the treatment end, in particular the handpiece, and with the illuminating light source being provided in elements or components which are further away from the treatment end of the apparatus. This is particularly advantageous because the end pieces at the treatment end, especially the handpiece, frequently have to be sterilized, at least in medical fields, In this case it is advantageous for sensitive elements or elements which are difficult to sterilize to be located in an area which does not need to be sterilized as regularly.

This element for injecting or coupling-in the illuminating light is preferably designed such that the processing or treatment beam can also be injected via the same optical element, so that this element is also an optical multifunction element for the purposes of this invention.

What has been stated above applies to an even greater extent to the arrangement of the laser light source in the laser treatment appliance, since the laser light source generally comprises complex and hence sensitive apparatuses, so that these are preferably arranged in "rear" components, that is to say at a distance from the treatment end.

However, in another embodiment, it is also possible for the component itself to have the illuminating light source and/or the laser light source. This may be the case especially in apparatuses where, for example, a simple diode laser can be used as the laser light source. However, it is also possible for such a component to be a component which is a relatively long way away from the treatment end of the laser treatment appliance, so that there are no problems in providing the illuminating light source and/or the laser light source in this component.

The advantages of the present invention are in particular highly important when the component is a handpiece, that is to say the treatment end piece of a laser treatment appliance, since both the treatment laser beam and the illuminating light must be available, in this area, in all cases. A handpiece such as this is designed such that especially the treatment end optical elements are in the form of optical multifunction elements. These optical multifunction elements are used especially in this end area shortly in front of the area to be treated, which also leads to highly effective illumination in the same direction. In this context, "illumination in the same direction" should be understood as meaning that both the treatment laser beam and the visible light for illumination are transmitted to the area to be treated essentially from the same direction and at least partially overlapping, thus very largely, or even completely, avoiding shadowing.

The invention preferably provides for at least the last of the first optical elements in the direction of the course of the treatment laser beam to be in the form of a multifunction element. This last optical element is generally the outlet window as described above.

In a further particularly preferred embodiment, at least the last of the first optical elements, which still influences the course of the treatment laser beam, is in the form of an optical multifunction element. This ensures that this last optical element which steers or influences the treatment laser beam, for example a mirror or a lens, is at the same time also used for illumination, thus ensuring the effect, as described, above of emission in the same direction and effective illumination without shadowing.

The invention also relates to a laser treatment appliance having an illumination system for use in the field of medicine, having a laser light source and an illuminating light source, with the illumination system and at least one optical element for the treatment laser beam being in the form of an optical multifunction element, such that the visible, preferably white light for illumination, is also steered via this at least one optical multifunction element.

The advantages of such a laser treatment appliance with an illumination system correspond to those which have been explained in conjunction with the component according to the invention, with the laser treatment appliance preferably having a component as has been described above.

A "white light-emitting diode" may also be provided as an illuminating light source, which combines light at different wavelengths (in particular a combination of a red, a green and a blue LED), so that the desired uniform white illumination is ensured. A "white light-emitting diode" such as this avoids the speckles described above which occur with monochromatic laser light, for example with the pilot beams explained above. Furthermore, standard illuminating light sources, for example incandescent lamps or glow lamps, may be used.

DESCRIPTION OF THE DRAWING

These and further characteristics and advantages of the present invention will be explained in more detail with reference to the schematic drawings below, in which:

FIG. 3 shows a third embodiment of a laser treatment appliance according to the invention.

DESCRIPTION OF THE PREFFERED EMBODIMENTS

Figure 1:
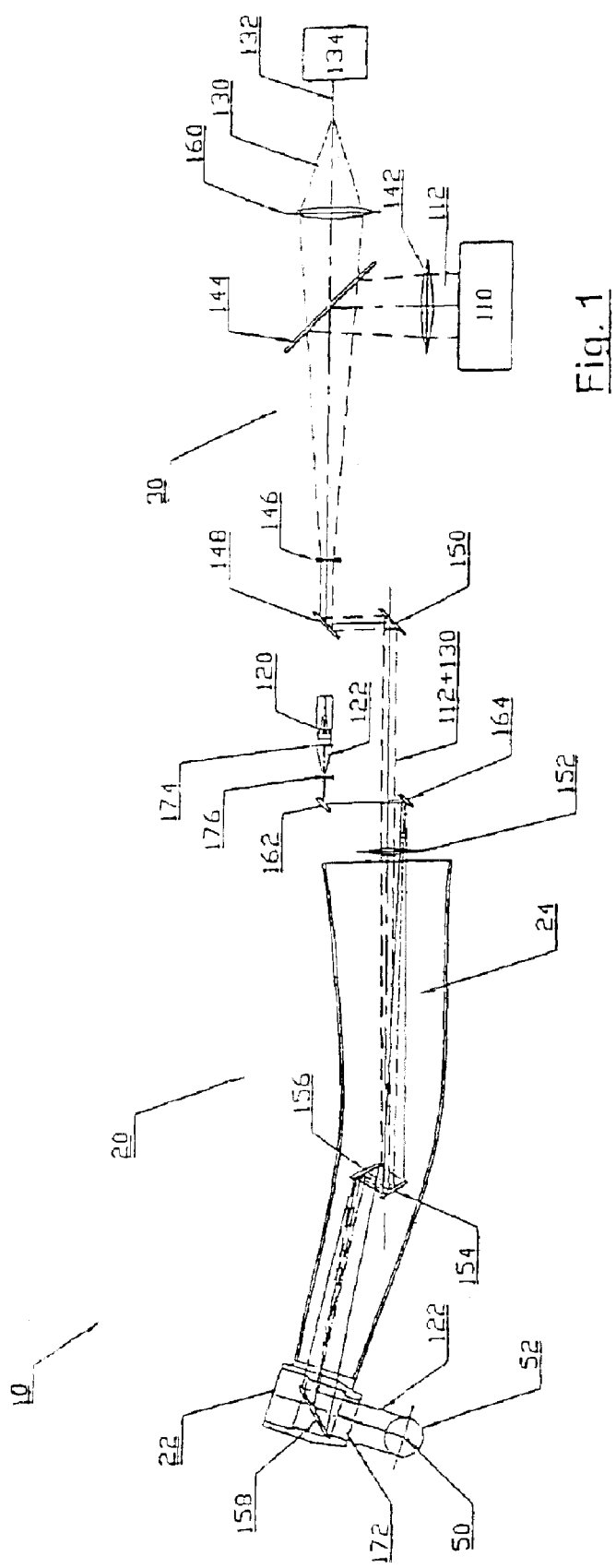
FIG. 1 shows a first embodiment of a laser treatment appliance according to the invention.

FIG. 1 shows, schematically, a first embodiment of a laser treatment appliance 10 according to the invention, with a component 20 and a component 30 of the laser treatment appliance 10. The component 20 is the handpiece, which does not specify the boundaries of the component 30 in more detail, may be fitted directly to the handpiece 20 or else may also be at a distance from it, in which case further components, which are not shown in FIG. 1, may be provided between the components 20 and 30.

At this point, it should be noted that FIG. 1 illustrates the components 20 and 30 only schematically, and that all the components 20,30 and possibly further components are connected to one another in one operating state.

The laser light source 110 emits a treatment laser beam 112, which is guided via a system of first optical elements by the component 30 and the handpiece 20 to an area 50 that is to be treated. In the process, the treatment laser beam 112 passes through a focussing lens 142, is reflected by a chromatic mirror element 144 at an angle of about 90°, then passes through a lens 146, and is then aimed by two further mirrors 148 and 150 in the direction of the handpiece 20. The mirrors 148 and 150 can move and form a scanning apparatus, so that the processing laser beam can be steered such that it scans a predetermined pattern in a predetermined time on the surface to be treated. In principle, it is also possible to provide a mirror mounted in a fixed position and only one mirror moving about two axes instead of the two moving mirrors 148 and 150, which can each be pivoted about one axis, and with these pivoting axes being arranged essentially at right angles to one another.

The treatment laser beam 112 reflected by the mirror 150 is guided via a lens 152, which is itself part of the handpiece 20 in an interior 24 of the handpiece 20, in which the treatment laser beam 112 is guided freely. In principle, it is also possible for the lens 152 not to be part of the handpiece 20 but to be part of a coupling or of an element which is arranged in front of the handpiece.

Since the handpiece 20 is designed to be curved in the direction of its treatment end in order to achieve better ergonomic handling, two further mirrors 154 and 156 are provided in the interior 24 of the handpiece 20, steering the treatment laser beam 112 onto a mirror 158 which is located in the head part 22 of the component 20. The mirror 158 is the last light-steering optical element, which steers the treatment laser beam 112 through a light outlet window 172 onto the area 50 to be treated.

The light outlet window 172 is also an optical element for the purposes of the invention, but with this optical element essentially having no influence on the profile of the treatment laser beam 112.

The embodiment of the laser treatment appliance 10, as illustrated in FIG. 1, furthermore has an illuminating light source 120, which, in this embodiment, is formed by a white light-emitting diode.

The first optical elements 152, 154, 156, 158 and 172 as explained above are thus in the form of optical multifunction elements which, in addition to the treatment 20 laser beam 112, also pass on the visible light 122 for illumination.

At this point, it should be noted that the treatment laser beam 112 and the visible light 122 do not influence one another, since they are at different wavelengths. The optical multifunction elements 152, 154, 156, 158 and 172 are in this case designed such that they have a comparable influence both on the light at the wavelength of the treatment laser beam 112 and on the light at the wavelength of the visible light, that is to say the mirrors 154, 156,158 are reflective for both wavelengths or wavelength bands, while the lens 152 and the light outlet window 172 are designed to be transmissive for both wavelengths.

Widely differing lasers may be used as the laser light source 110, even pulsed lasers, which preferably emit light at a wavelength between 900 nm and 1100 nm, and preferably 1030 nm or 1064 nm. However, the laser light source 110 is in no way restricted either to a specific wavelength or to a specific laser system.

The desired laser system and the desired wavelength of the treatment laser beam, which is emitted by the laser light source 110, are critically dependent on the desired purpose of use. It should also be noted at this point that the expression laser light source 110, which is illustrated only schematically in FIG. 1, should also be understood as referring to a complex system with a number of lasers, for example including pump lasers. The laser light source 110 may also have frequency converters or different further optical elements.

The illuminated light source 120 (in this case a standard incandescent lamp) is arranged (seen in the emission direction) parallel to the treatment laser beam 112, with the visible light 122 passing through a lens 174 and a further lens 176 for illumination from the illuminating light source 120, and then be injected by two mirrors 162 and 164 into the lens 152 of the handpiece 20. The lenses 174 and 176 in this embodiment of the illuminating light provide the appropriate divergence and thus control the desired diameter in order to illuminate the working area as desired.

The lens 152 is thus the first optical multifunction element, which is used both for steering and for influencing the treatment laser beam 112 as well as for steering the visible light 122.

The mirrors 162, 164, 154, 156 and 158 are in this case designed such that, although the visible light 122 is injected essentially parallel to the treatment laser beam 112 via the lens 152 into the handpiece 20, the treatment laser beam 112 and the visible light 122 are steered in the same direction by the mirror 158 onto the area 50 to be treated.

The treatment laser beam 112 is very highly focussed, while the visible light 122 illuminates an illuminated area 52, which is essentially circular, with the centerpoint of the circle essentially being coincident with the area 50 to be treated. The size of the illuminated area 52 may be chosen as required, depending on the application, and in the field of dentistry this area 52 will have a diameter of about 5–10 mm, and preferably 6 mm.

The embodiment of the laser treatment appliance 10 as illustrated in FIG. 1 has the advantage that, in addition to processing and treatment, it can also be used for diagnosis or analysis of the area to be treated, or for analysis during treatment.

Especially in the field of dentistry, it is possible to spectroscopically investigate the plasma which is produced during the removal of tooth material, without having to provide an additional laser light source.

In the embodiment shown here, the radiation 130, which is produced by the plasma, and is also referred to as spectroscopy light, is passed to the mirror 144 from the area to be treated in the rearward direction via the optical elements 172, 158, 156, 154, 152, 150, 148, 146. The mirror 144 is in this case designed such that it is essentially translucent for the broadband spectrum of the spectroscopy light, so that the radiation 130 and the spectroscopy light are passed through the mirror 144 to a lens 160, which focusses the radiation 130 or the spectroscopy light and feeds it via an optical fiber 132 to an optical evaluation unit, in this case to a spectrometer 134.

The spectroscopy light or the radiation 130 is evaluated in the spectrometer 134, and evaluation units, for example computers, or the like which may, of course, be connected to the spectrometer for this purpose.

With regard to a handpiece which allows such spectroscopy, reference is made to the parallel application (official file reference 101 15 426.7), whose entire contents are included in this application, by reference.

A further advantage of the embodiment illustrated in FIG. 1 is that the illuminating light is not passed via the mirrors 148, 150, which are in the form of a scanner, so that the illuminating light is not influenced by them. This therefore avoids any possible flickering of the illuminating light. The same is true for the embodiments shown in FIGS. 2 and 3.

Figure 2:
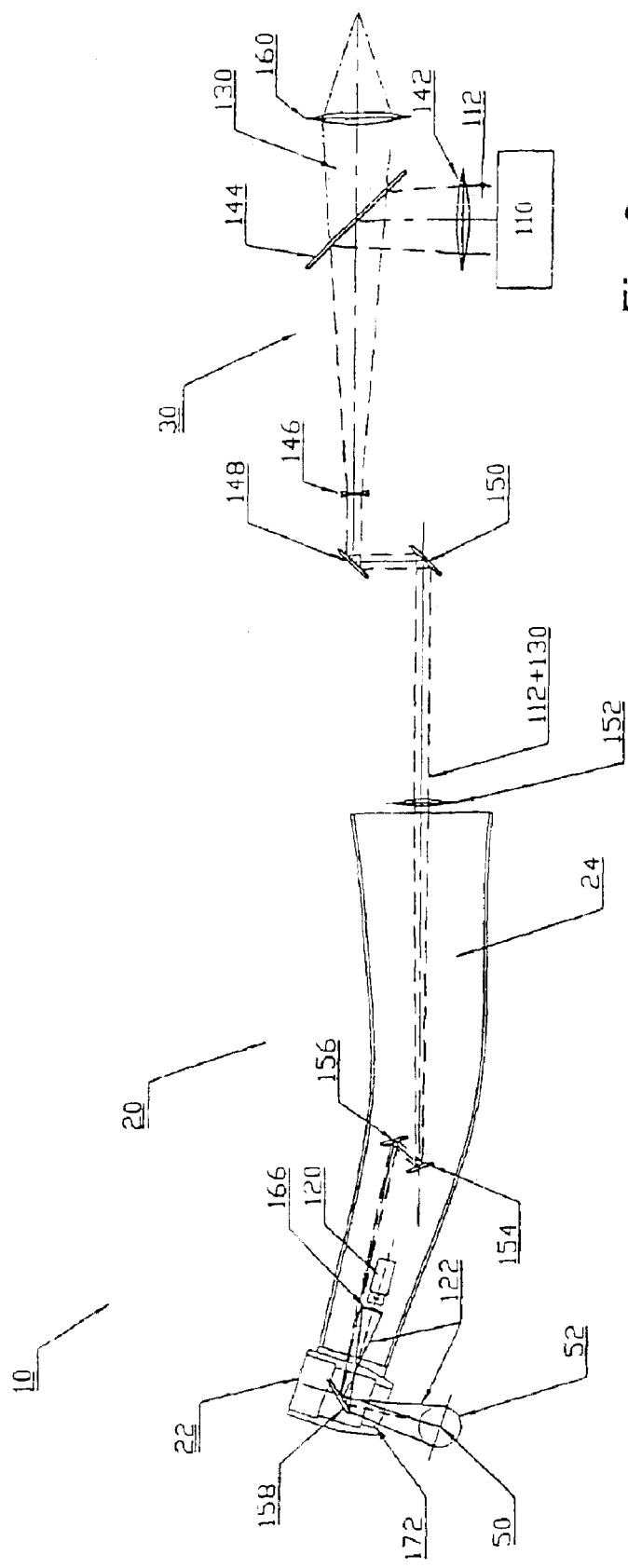
FIG. 2 shows a second embodiment of a laser treatment appliance according to the invention.

FIG. 2 shows a further embodiment of a laser treatment appliance 10 according to the invention. The same or similar elements are provided with identical reference symbols.

The treatment laser beam 112 emitted from the laser light source 110 passes through the laser treatment in an analogous manner to that which has been described in conjunction with FIG. 1.

In contrast to the embodiments shown in FIG. 1, in the embodiment of the laser treatment appliance 10, as shown in FIG. 2, the illuminating light source 120 is arranged in the handpiece 20 itself, with the emitted visible light 122 passing through a lens 166 before being passed to the mirror 158, which reflects the visible light 122 such that it illuminates the area 52. In this embodiment, only the mirror 158, that is to say the last light-steering or light-influencing optical element, and the light outlet window 172 are in the form of optical multifunction elements, which pass on both the treatment laser beam 112 and the visible light 120 for illumination. In this particularly advantageous embodiment, only the last elements 158, 172 at the treatment end are thus in the form of optical multifunction elements. Owing to the arrangement of the illuminating light source 120 in the area of the treatment end of the handpiece 20, virtually no additional optical elements are required exclusively for the visible light 122 in this embodiment. The only second optical element which is provided exclusively for the visible light 122 is the lens 166.

The spectroscopy which has been explained in conjunction with FIG. 1 is also possible with this embodiment, and in this context reference is made to the description relating to FIG. 1, in order to avoid repetitions.

Yet another embodiment of the laser treatment appliance 10 according to the invention is illustrated in FIG. 3, with this embodiment being the most similar to the embodiment shown in FIG. 2.

In the embodiment shown in FIG. 3, the illuminating light source 120 (in this case once again an incandescent bulb) is also accommodated in the handpiece 20, with the visible light 122 for illumination not being guided freely, at least initially, but being steered via an optical fiber 168 into the vicinity of the head part 22.

In this embodiment, the optical fiber 168 consists of a fiber pack, which ends shortly in front of the head part 22 in an essentially annular fiber bundle end 170, in whose interior the treatment laser beam 112 runs. In principle, of course, it is also possible to provide a circular fiber bundle, with essentially the entire area of the circle being filled with fiber ends. In this case, this circular fiber bundle ends parallel to the treatment laser beam.

The visible light 122 for illumination is steered or directed from the fiber bundle end 170 via the mirror 158, which is in the form of an optical multifunction element, to the area 52 to be illuminated, passing through the outlet window 172.

In this embodiment as well, at least the mirror 158 and the light outlet window 172 are in the form of optical multifunction elements, so that this results, in particular, in illumination which is in the same direction as that in which the treatment laser beam 112 runs, hence ensuring shadow-free illumination of the area 50 to be treated. Furthermore, the sensitive optical fiber 168 and the sensitive fiber bundle end 170 are arranged entirely in the interior 24 of the handpiece 20, so that they are protected against external influences, and hence against damage.

Those skilled in the art will be able to implement further possible embodiments, in particular combinations of the embodiments illustrated in FIGS. 1 to 3, without having to depart from the subject matter of the invention. Depending on the field of application, those skilled in the art will be able to design the laser treatment appliance and the individual components in accordance with the requirements.

The embodiment illustrated in FIG. 1 has the advantage that the handpiece component t- does not contain any live parts and, does not contain any excessively sensitive or expensive optical components, so that this firstly ensures high reliability during operation.

The embodiment shown in FIG. 3 has, in particular, the advantage that a number of light sources can also be arranged in an annular shape around the axis of the treatment laser beam 112, in which case the light from the number of light sources can be carried in individual optical waveguides or in individual optical fibers in the optical waveguide 168. An annular arrangement of a number of illuminating elements such as this can in principle also be used in all the other described embodiments.

A straight handpiece may, of course, also be used instead of the ergonomic, curved embodiment of the handpiece as shown in all the figures. In particular, it is also possible to emit the treatment laser beam as well as the visible light for illumination in the axis direction of the element at the treatment end, that is to say not, as described in the embodiments, at an angle of 90°, although a configuration such as this is particularly advantageous for dentistry treatment. Other angular arrangements are, of course, also feasible, varying depending on the field of use and application.

Finally, it should also be mentioned that, in principle, it is also possible to equip the laser treatment appliance with a pilot laser in addition which, as explained above, can be used as an "aiming apparatus". In principle, it is also possible to provide a further monochromatic light source (diagnosis laser beam) in the laser treatment appliance if, for example, it is desirable to use fluorescence to analyze the material to be treated. The monochromatic light for producing the fluorescence may likewise, if desired, be passed and steered via the optical elements and via the multifunction elements according to this invention. A combination of a laser as a pilot laser and as a diagnosis laser is also feasible, since fluorescence can also be stimulated by a laser beam which emits in the visible wavelength band.

The features which have been disclosed in the present description, the claims and the drawings may be important to the implementation of the invention, in its various embodiments, both individually and in any given combination.

What is claimed is:

1. A laser treatment appliance having an illumination system for use in the field of medicine, includes a laser light source for producing a treatment laser beam, which is guided essentially freely, an illuminating light source for producing a visible light for illuminating an area to be treated, and one or more optical elements via which the treatment laser beam is passed on, at least one of said optical elements being in the form of an optical multifunction element such that the visible light for illumination is also directed at least over this at least one optical multifunction element, further including a means for diagnosis or analysis of radiation which is produced during and by the treatment process, said at least one optical multifunction element also influencing said treatment laser beam and the visible illuminating light by an equivalent reflecting and/or transmitting manner, further including a beam splitter, which extends at least over the entire cross section of the treatment laser beam, for outputting the radiation, and which is arranged between the laser light source and the at least one optical multifunction element in the incidence direction of the treatment laser beam such that the visible light from the illuminating light source does not pass through it.

2. The laser treatment appliance as claimed in claim 1, wherein said appliance has an additional optical element which is essentially in the form of a light outlet window which transmits the laser treatment light and does not significantly influence the profile of the treatment laser beam.

3. The laser treatment appliance as claimed in claim 2, wherein said light outlet window is in the form of an optical multifunction element.

4. The laser treatment appliance as claimed in claim 1, wherein said appliance has at least one optical element, which influences the profile of the treatment laser beam.

5. The laser treatment appliance as claimed in claim 4, wherein said at least one of the optical elements which influence the treatment laser beam is in the form of an optical multifunction element.

6. The laser treatment appliance as claimed in claim 5, wherein said at least one of the optical elements which influence the treatment laser beam is a mirror element.

7. The laser treatment appliance as claimed in claim 5, wherein said at least one of the optical elements which influence the treatment laser beam is a focusing lens.

8. The laser treatment appliance as claimed in claim 1, wherein said appliance has a component which itself comprises an illuminating light source.

9. The laser treatment appliance as claimed in claim 8, wherein said component is a handpiece at the treatment end.

10. The laser treatment appliance as claimed in claim 9, wherein said handpiece directs the visible light for illumination to emerge from said handpiece essentially in the same direction as the treatment laser beam.

11. The laser treatment appliance as claimed in claim 1, wherein the beam axis of the treatment laser beam and the beam axis of the visible light for illumination are offset with respect to one another at least in the optical multifunction element in the direction of the light emission.

12. The laser treatment appliance as claimed in claim 1, wherein a white light-emitting diode or an incandescent lamp is provided as the illuminating light source.

* * * * *